United States Patent [19]

Ryland et al.

[11] Patent Number: 5,169,399
[45] Date of Patent: Dec. 8, 1992

[54] ACETABULAR CUP IMPACTOR

[75] Inventors: Genevieve A. Ryland; Duane G. Snyder, both of Warsaw, Ind.

[73] Assignee: Boehringer Mannheim Corporation, Indianapolis, Ind.

[21] Appl. No.: 778,509

[22] Filed: Oct. 17, 1991

[51] Int. Cl.$^5$ .............................................. A61F 2/32
[52] U.S. Cl. .................................. 606/91; 606/99
[58] Field of Search ................... 606/91, 99, 104; 623/20; 269/47, 48, 48.2, 48.3, 157, 217, 229; 29/275

[56] References Cited

U.S. PATENT DOCUMENTS

| | | | |
|---|---|---|---|
| 472,311 | 4/1892 | Mcintyre | 269/229 |
| 614,724 | 11/1898 | Jennings | 269/229 |
| 627,669 | 6/1899 | Jenkins | 269/229 |
| 1,152,239 | 8/1915 | Thom | 269/229 |
| 2,271,012 | 1/1942 | Hutchings | 269/48.2 |
| 2,420,020 | 5/1947 | Snell | 269/229 |
| 4,870,747 | 10/1989 | Maack | 269/229 |
| 5,048,805 | 9/1991 | Wiseman | 269/48.4 |
| 5,059,196 | 10/1991 | Coates | 606/99 |

OTHER PUBLICATIONS

"Discover": Discover the Next Generation in Acetabular Technology, Surgical Technique, pp. 1-14, date unknown.
"McCutchen Hip Surgical Technique", Dow Corning Wright, pp. 1-10, date unknown.
H Dunn, M.D., "Surgical Technique for Primary Hip Arthroplasty", Univ. of Utah College of Medicine, Salt Lake City, Utah, pp. 1-19, date unknown.
D. Hungerford, M.D. et al., "The P.C.A. Primary Hip System Surgical Technique", Howmedica Surgical Techniques, pp. 1-6, date unknown.
R. Turner, M.D. et al., "The Howmedica Precision Hip System", pp. 1-6, date unknown.

*Primary Examiner*—Michael A. Brown
*Attorney, Agent, or Firm*—Barnes & Thornburg

[57] ABSTRACT

An assembly (10) for positioning a prosthetic acetabular cup assembly (110) in a patient's hip is provided. The assembly (10) includes a bearing component (114) having an inner bearing surface (134) for receiving a femoral ball and an outer surface (132) attachable to a shell component (112) The shell component (112) is attached to an acetabulum to replace a natural hip socket. The shell component (112) includes an inner surface (120) defining a cavity (126) for receiving the outer surface (132) of the bearing component (114) therein. The assembly (10) includes a handle (12) attached to a split head (30). The split head (30) is divided into first and second gripping elements (36, 38) that jointly form a gripping surface to engage the inner bearing surface (134) of the bearing component (114). The assembly (10) holds the bearing component (114) at a selected orientation with relation to the shell component (112), and is used to drive the bearing component/shell component (114/112) into the acetabulum.

26 Claims, 2 Drawing Sheets

ACETABULAR CUP IMPACTOR

BACKGROUND AND SUMMARY OF THE INVENTION

The present invention relates to an apparatus for positioning prosthetic cup assemblies or parts thereof in a patient. More particularly, the present invention relates to gripping head useful for holding an acetabular cup assembly while the acetabular cup assembly is inserted into position in a hip of a patient.

Prosthetic cup assemblies that replace diseased, damaged, or degraded bone are known. In one common operation, the acetabulum of a hip is partially replaced with an acetabular cup assembly that includes a metal shell component for attachment to an acetabulum to replace the natural socket. A polymeric bearing component is disposed in the metal shell component to provide a hemispherical bearing surface for receiving a femur ball prosthesis element. Often, the polymeric bearing component is nonsymmetrical, having a built-up lip around a portion of the hemispherical bearing surface to help prevent dislocation of an installed femur ball from the hemispherical bearing surface. In addition, the bearing can be inserted into the shell after the shell is already in place in the acetabulum. Additionally, a one-piece polymeric acetabular component can be cemented into the cavity without any accompanying metal shell.

Proper positioning of the acetabular cup assembly usually requires reaming of the acetabulum to define a suitable bone cavity, followed by implantation of the shell component and, in some cases, subsequent fixation of the bearing component to the shell component. During installation of the hemispherical bearing component, the surgeon selects an orientation of the bearing with respect to the shell component to align the lip of the nonsymmetrical bearing component in the most advantageous position to reduce the likelihood of dislocation of the femur ball. A positioning/impactor device is necessary to hold the bearing component at a selected orientation with relation to the shell component, and allow a orthopaedic surgeon to drive the bearing component into attachment with the shell component.

The present invention provides for an apparatus for positioning a bearing component of a prosthetic acetabular cup assembly in a patient's hip. Typically, the bearing component includes an inner bearing surface for receiving a femoral ball and an outer surface attachable to a shell component. The shell component, which may be found of generally composed of titanium and have a bone growth promoting outer surface, is attached to an acetabulum to replace a natural hip socket. In one embodiment, the shell component also includes an inner surface defining a cavity for receiving the outer surface of the bearing component therein. The positioning apparatus includes a handle attached to a split head. The split head can be attached to extend parallel and collinear with respect to the handle, or can alternatively be attached so that it extends at a some predetermined angle relative to the longitudinally extending handle. The latter attachment position of the split head is particularly valuable for use in conjunction with asymmetric bearing components, and the former for use with symmetric bearing components. The split head is divided into first and second gripping elements that jointly form a gripping surface to engage the inner bearing surface of the bearing component.

A spring is attached to one of the first and second gripping elements. The spring is biased to urge separation of the first and second gripping elements. A lever arm attached to one of the first or second gripping elements can be moved to oppose the spring bias and move the first and second gripping elements closer together to allow positioning of the split head in contact with the inner surface of the bearing component.

In preferred embodiments the split head is configured to present a generally hemispherical surface. The first and second gripping elements are formed by hemisection (division in half) of the hemisphere, providing two gripping elements that are substantially mirror images of each other. Encircling the split head is a first gripping ridge defined to promote frictional engagement of the split head with the inner bearing surface of the bearing component. Optionally, additional gripping ridges can defined in the split head to promote engagement of the split head with differently sized bearing components, whether larger or smaller.

These ridges, as will be more fully described hereinafter, are proportioned to hold the plastic bearing component for forcible insertion into the affixed shell. Preferably, the plastic bearing component, or the assembled plastic bearing component and shell component, are held so that the plastic bearing component is not stressed during insertion into an acetabular bone cavity.

Typically, the spring is biased to hold the gripping elements apart from each other. Before the split head can be inserted to contact the inner bearing surface of the bearing component, the spring biasing force must be overcome to bring the gripping elements together. In preferred embodiments, the first gripping element of the split head is fixedly held relative to the handle, and the second gripping element is movable, usually by pivot action about a pivot pin, with respect to the handle. A moving means, such as a lever arm is attached to the second gripping element of the split head, and movement of the lever arm facilitates movement of the second gripping element toward the immobile first gripping element.

Another aspect of the present invention relates to the coupled attachment of the split head to the handle. In a preferred embodiment, the split head is provided with internal threads capable of threadingly engaging external threads defined on the handle. In other embodiments, a declination adaptor can be used to angle the split head with respect to the handle. A body of the declination adaptor includes internal threads to engage the external threads of the handle, and external threads to engage the internal threads of the split head. The external threads of the body are directed at a non-parallel angle relative to the internal threads of the body, in effect canting the attached split head relative to the handle. This is particularly useful for insertion of asymmetric bearing components, since a declination adaptor with an appropriate angle can be selected to match the degree of asymmetry of the bearing component.

Additional objects, features, and advantages of the invention will become apparent to those skilled in the art upon consideration of the following detailed description of a preferred embodiment exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
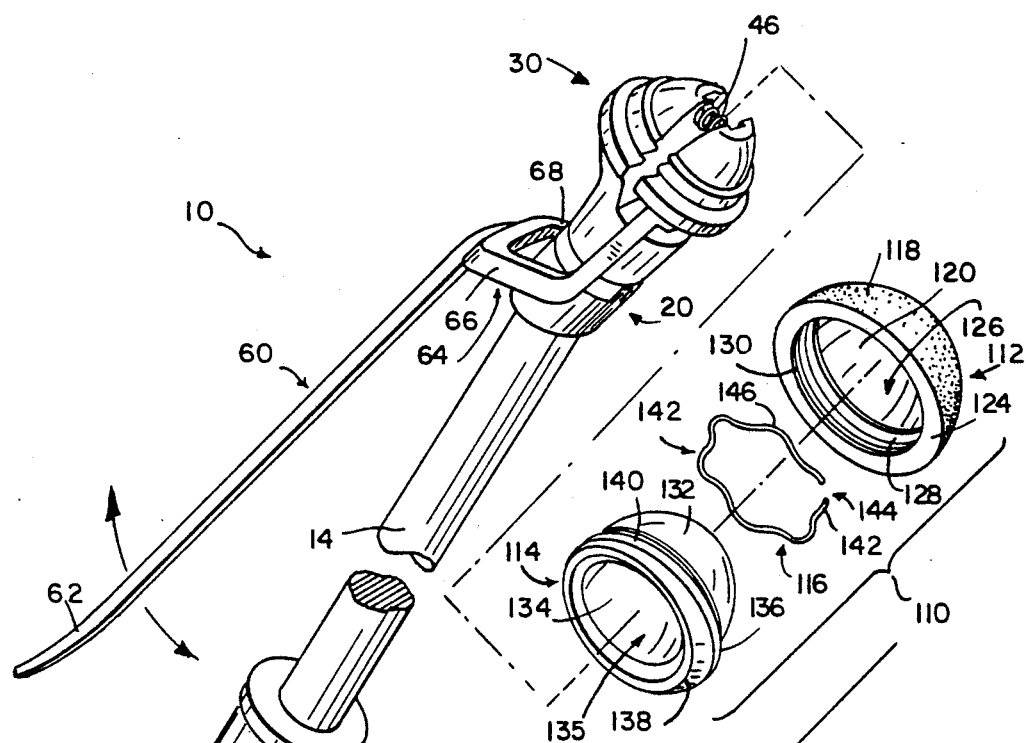
FIG. 1 is an exploded perspective view of a preferred embodiment of the present invention illustrating an acetabular cup impactor suitable for engaging and properly positioning an acetabular cup assembly.
Figure 2:
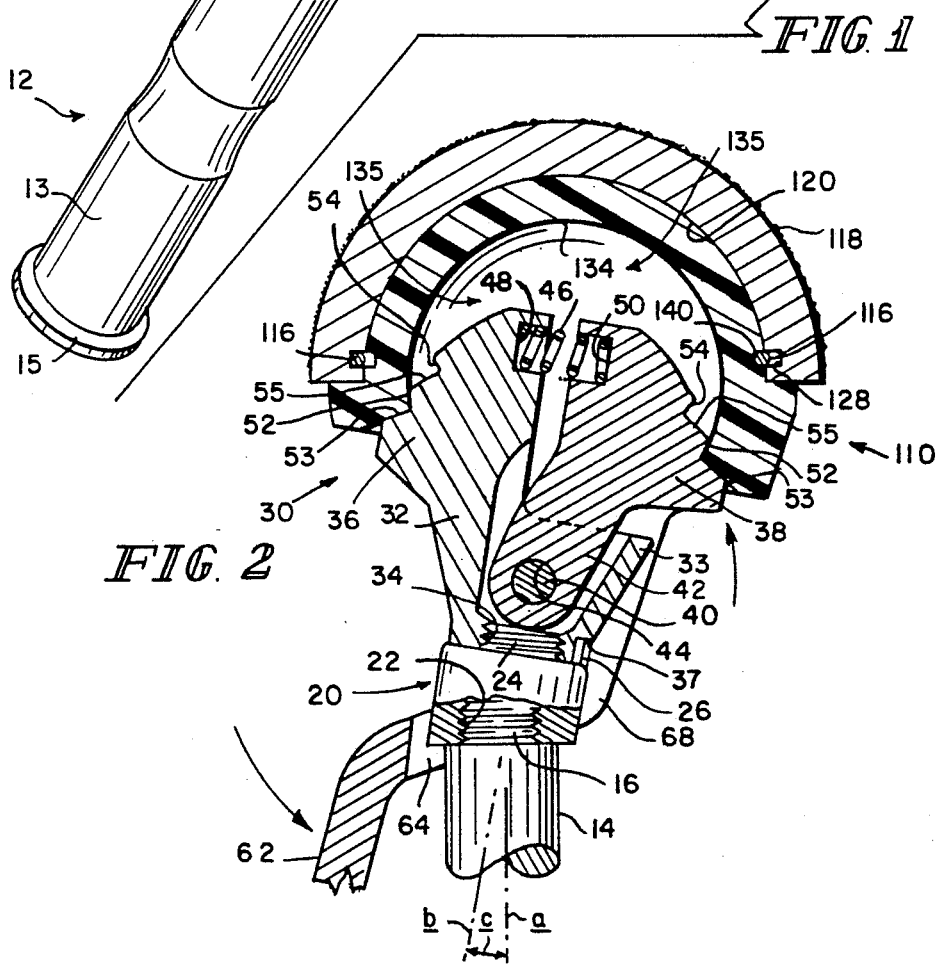
FIG. 2 is a side, cross sectional view illustrating a split head of the acetabular cup impactor engaging a bearing component of the acetabular cup assembly. The split head is attached at an angle to a handle by an intervening declination adaptor.

Referring now to the drawings, FIGS. 1 and 2 illustrate an acetabular cup impactor assembly 10. The assembly 10 includes a handle 12 connected to a split head 30 by way of a declination adaptor 20. A movable lever arm 60 is attached to the split head 30. In operation, the split head 30 holds onto an acetabular cup assembly 110, shown disassembled.

The longitudinally extending handle 12 includes a manual grip 13, slightly contoured to increase ease of holding the assembly 10, and an extension piece 14. An impactor plate 15, formed from a flat steel disk, is permanently attached to one end of the manual grip 13. The manual grip 13 is constructed of a dense polymeric material that is permanently attached to the extension piece 14. The extension piece 14 is rigidly constructed of steel or other metal, and longitudinally extends collinear to the manual grip 13. The extension piece 14 defines external threads 16 at its terminal end opposite the handle 12. The handle 12 is designed to allow transfer of force applied perpendicular to the surface of the impactor plate 15 through the manual grip 13, extension piece 14, declination adaptor 20, split head 30, to the acetabular cup assembly 110.

The declination adaptor 20 is formed to define internal threads 22 extending along axis a and external threads 24 extending along axis b. Axis b is canted at an angle c (about 10 degrees) relative to axis a. The internal threads 22 threadingly engage the external threads 16 of the extension piece 14, and the external threads 24 threadingly engage internal threads 34 defined in a split head support 32 of the split head 30. A lug 26 is inserted into a notch 37 defined in the split head support 32 to prevent rotation of the declination adaptor 20.

Figure 4:
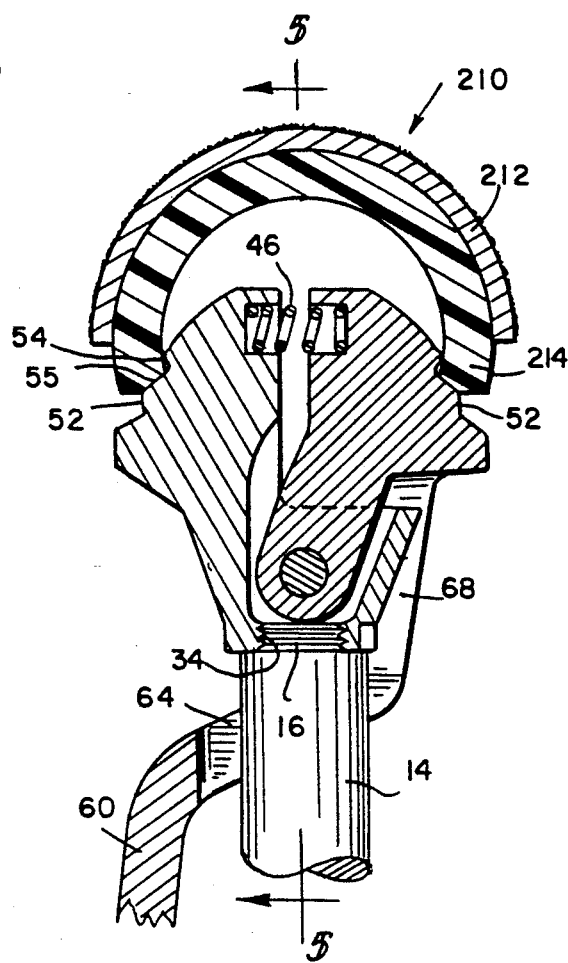
FIG. 4 is a side, cross sectional view of the split head directly attached to a handle without the intervening declination adaptor. In this view a symmetrical acetabular cup assembly dimensioned smaller than that shown in FIGS. 1 and 2 is shown held by engagement with a second gripping ridge.
Figure 5:
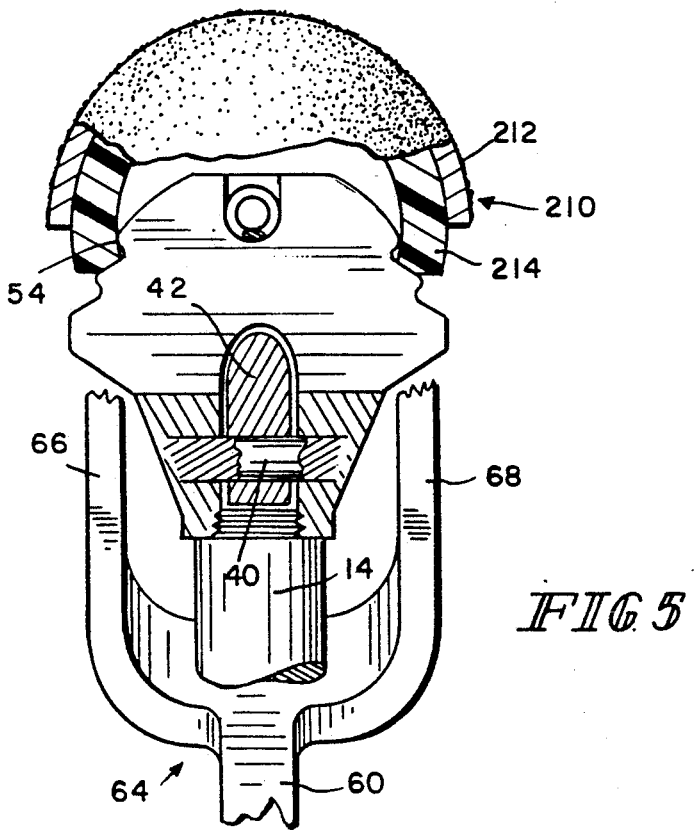
FIG. 5 is a view along section 5—5 of FIG. 4, illustrating the position of a yoke of a lever arm and the split head gripping the smaller bearing component.

The split head 30 includes a first gripping element 36 integrally formed with and supported by the split head support 32. Positioned adjacent to the first gripping element 36 is a second gripping element 38. Taken together, the gripping elements 36 and 38 form a generally hemispherical surface that can be inserted into bearing component 114 of the acetabular cup assembly 110. To frictionally grip and hold the cup assembly 110, first and second gripping ridges 52 and 54 are defined on the split head 30. The gripping ridges 52 and 54 respectively encircle the combination of gripping elements 36 and 38 to give annular offset contact surfaces capable of engaging differently sized acetabular cup assemblies. As shown in FIG. 2, acetabular cup assembly 110 is primarily held by action of the first gripping ridge 52. Use of the second gripping ridge 54 to hold a smaller inside diameter acetabular cup assembly is illustrated in FIGS. 4 and 5.

The split head 30 is normally biased to remain open, with the second gripping element 38 moving outward with respect to the fixed first gripping element 36 in response to the outward force of an expansion spring 46 situated in cavities 48, 50 defined in the gripping elements 36, 38. The second gripping element 38 is supported to pivot about a pivot pin 40 by a pivot arm 42. The pivot arm 42 has defined therein a hole 44 through which the pivot pin 40 is inserted and the first gripping element 36 is attached to the pivot pin 40 via the pivot pin passing through the splint head support 32 and onto the first gripping element 36. The pivot pin 40 may be permanently, and immovably, attached to the split head support 32. This arrangement allows a limited outward swinging movement of the second gripping element 38 in response to action of the spring 46. However, only a limited outward movement is permitted, because the motion of the pivot arm 42 is blocked by wall 33 of the split head support 32.

Bringing together the first and second gripping elements 36 and 38 is accomplished by manually pushing or pulling movable lever arm 60 closer to handle 12 of the assembly 10. The movable lever arm 60 includes a lever arm handle 62 and a yoke 64. The yoke 64 splits to form a first yoke arm 66 and a second yoke arm 68. The yoke arms 66, 68 are attached to the split head 30. Movement of the lever arm handle 62 toward the handle 12 acts to move the second gripping element 38 closer to the first gripping element 36, with the pivot pin 40 acting as a fulcrum. When the two gripping elements are brought close together, the split head 30 can be inserted into the acetabular cup assembly 110. Release of the lever arm 60 allows the second gripping element 38 to move away from the first gripping element 36, in effect causing the first gripping ridge 52 of the split head 30 to engage and hold the acetabular cup assembly 110.

FIGS. 1 and 2 also illustrate the acetabular cup assembly 110 in a disassembled state (FIG. 1) and in a fully assembled configuration (FIG. 2). The acetabular cup assembly 110 includes a shell component 112 designed to be affixed to the acetabulum of a patient to replace the natural hip socket and a bearing component 114 designed to be inserted into shell component 112. A lock wire 116 is also provided to retain the bearing component 114 within the shell component 112. The shell component 112 includes an outer surface 118 which can be textured to facilitate securement of the shell component 112 in place within an appropriately prepared acetabulum. Shell component 112 is preferably made from titanium, but may be made from a cobalt chrome material. Shell component 112 also includes a generally hemispherically shaped inner surface 120. Shell component 112 includes a rim 124. The rim 124 defines a plane through which bearing component 114, held by the split head 30 of the acetabular cup assembly 110, enters cavity 126 of shell component 112 formed by inner surface 120. Inner surface 120 of shell component 112 is formed to include an arcuate groove 128 therein. The arcuate groove 128 extends around the entire periphery of cavity 126 spaced apart from rim 124 by a predetermined distance.

Shell component 112 is also formed to include anti-rotation lugs 130 on inner surface 120 of shell component 112. In the embodiment of the acetabular cup assembly 110 illustrated, four lugs are provided. The lugs 130 are situated below the arcuate groove 128 formed in the inner surface 120 of the shell component 112. The lugs 130 interfere or machine into the outer surface of the bearing component as the bearing component 114 is inserted into the shell component 112 to prevent rotation of the bearing component relative to the shell component. There are no preformed slots in the bearing component for receiving the lugs. This feature advantageously provides no clearance or tolerance between the lugs and the outer surface of the bearing and prevents torsional backlash that can occur when there is clearance between the lug and preformed notches in the bearing component.

Bearing component 114 includes a generally hemispherically shaped outer surface 132 which is congruent or complimentary to inner surface 120 of shell component 12. Bearing component 114 also includes an inner bearing surface 134 for receiving a prosthetic femoral ball (not shown) and a radially outwardly projecting lip or flange 136 extending circumferentially around the bearing component 114. The bearing component 114 illustrated in the FIGS. 1-2 is a nonsymmetrical bearing component. It is understood, however, that the bearing component of the present invention may be a symmetrical component such as the bearing component 214 illustrated in FIGS. 4 and 5. Bearing component 114 shown in FIGS. 1 and 2 includes a built-up lip portion 138 extending away from the flange 136 to aid in the retention of the femur ball inside bearing surface 134. Bearing component 114 is also formed to include radially outwardly opening arcuate groove 140 spaced apart from flange 136 by the same predetermined distance that arcuate groove 128 is spaced apart from rim 124 of shell component 112. Bearing component 114 is preferably made from a polymeric material such as ultra-high molecular weight polyethylene (UHMWPE). Of course, the bearing component 114 could be made of other types of implantable bearing material.

A preferred embodiment for lock wire 116 is illustrated in FIGS. 1 and 2. Lock wire 116 is a serpentine shaped wire which is preferably made from cobalt chrome material and shaped by conventional wire forming techniques. Titanium may also be used to make wire 116. The lock wire 116 shown in FIGS. 1 and 2 has a somewhat hexagonal shape and includes six engaging sections 142. The wire 116 can be either serpentine shaped as shown in FIGS. 1 and 2 or polygon shaped having any number of sides. A gap 144 is provided between two adjacent sections 142 of lock wire 116 to permit lock wire 116 to expand radially outwardly. Corner portions 146 are situated between the side sections 142. The wire 116 may be conventionally heat treated to increase its strength. When assembled, lock wire 116 is inserted into the arcuate groove 128 of shell component 112. Corner portions 146 of the lock wire 116 remain inside arcuate groove 128 formed in shell component 112 to retain lock wire 16 inside the arcuate groove 128.

It will be understood by those skilled in the art that in addition to the foregoing described shell component/bearing components, other types of implant structures can alternatively be used in conjunction with an apparatus of the present invention. For example, single piece polymeric acetabular cups, multiple component cup assemblies, and other art recognized acetabular cup assemblies can be used.

In operation, either prior to or after fixation of shell component 112 to an appropriately prepared acetabulum, outer surface 132 of bearing component 114 is inserted into cavity 126 of shell component 112. When the bearing component 114 is fully inserted into the shell component 112, the corner portions 146 snap into place within arcuate groove 128, locking the bearing component 114 to the shell component 112. Since there are no preformed notches in outer surface 132 of bearing component 114 to receive lugs 130, the bearing component 114 can be inserted into shell component 112 at any desired orientation not limited by such preformed notches. Lock wire 116 therefore retains bearing component 114 inside shell component 112 regardless of the position of bearing component 114 relative to shell component 112. The surgeon positions the bearing component 114 in the most advantageous position 112 to reduce the likelihood that a femur ball (not shown) will become dislodged from the cavity 135 defined by inner surface 134.

The surgeon holds and positions the assembled acetabular cup assembly 110 (or the bearing component 114 when the shell component 112 is already installed in a patients's acetabulum) with the aid of the acetabular cup impactor assembly 10. To engage the bearing component 114, a surgeon inserts the split head 30 into the cavity 135 defined by the bearing component 114 while the movable lever arm 60 is depressed toward the handle 12. Once the split head 30 is positioned in the cavity 135, the movable lever arm 60 is released, causing the first and second gripping elements 36 and 38 of the split head 30 to move apart. As the gripping elements 36 and 38 move apart, the first gripping ridge 52 frictionally engages inner surface 134 of the bearing component 114.

While holding the manual grip 13 of the impactor assembly 10, a surgeon positions the coupled impactor assembly 10 and cup assembly 110 at a desired position relative to a patient's acetabulum. A mallet (not shown) or other hammering means is used to strike the impactor plate 15, driving the acetabular cup impactor toward the acetabulum. Since it is critical that cup assembly 110 retain its initial, undistorted configuration, this driving force is smoothly and evenly transmitted to the cup assembly 110 by contact with a first annular impact surface 53 and a second impact surface 55. The impact surfaces 53, 55 are positioned to extend substantially perpendicular to the first gripping 52, and lies in contact with the bearing component 114. The driving force is transferred from surface 53 to the bearing component 114, providing a substantially stress-free driving force that secures the cup assembly 110 in its proper position in the acetabulum of a patients hip.

Figure 3:
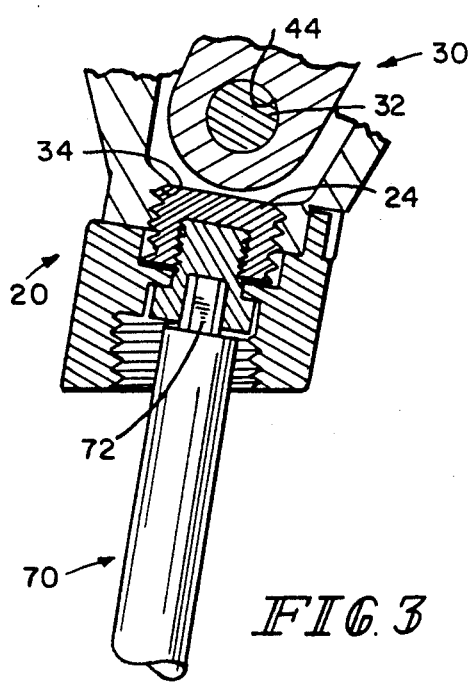
FIG. 3 is an enlarged, side view with portions broken away illustrating removal of a declination adaptor.

When operative conditions do not require canted or asymmetrical bearing components to reduce the chance of dislodgement of a femoral ball (not shown) from the acetabular cup assembly, the declination adaptor 20 can be removed and split head 30 directly attached to the extension piece 14. As shown in FIG. 3, removal of the declination adaptor 20 from its threaded attachment between the split head 30 and extension piece 14 first requires unscrewing the combination of the split head 30 and declination adaptor 20 from the extension piece 14. While holding the combination of declination adaptor 20 and split head 30, a tool 70 having a hex head 72 is inserted and rotated (direction of rotation indicated by arrow) to unscrew the external threads 24 of the declination adaptor 20 from engagement with internal threads 34 of the split head 30. As seen in FIGS. 4 and 5, the split head 30 is then directly attached to the extension piece 14 by screwingly engaging the external threads 16 of the extension piece 14 with the internal threads 34 of the split head 30.

FIGS. 4 and 5 illustrate holding engagement of the acetabular cup impactor assembly 10 (without declination adaptor 20) with an acetabular cup assembly 210. The acetabular cup assembly 210 has a shell component 212 comparable to that of previously described shell component 112, but having slightly smaller overall dimensions. Fitting into the shell component 212 is a symmetrically configured bearing component 214. The bearing component 214 is slightly smaller than bearing component 114, so that the smaller diameter second gripping ridge 54 (as compared to first gripping ridge 52) frictionally engages the bearing component 214. Operationally, placement of the acetabular cup assembly 210 follows the procedure previously noted for placement of acetabular cup assembly 110, with the exception that the substantially stress free driving force is transmitted through a second annular impact surface 55 to the cup assembly 210.

Although the invention has been described in detail with reference to several preferred embodiments, variations and modifications exist within the scope and spirit of the invention as described and defined in the following claims.

We claim:

1. An apparatus for positioning a prosthetic acetabular cup assembly in a patient's hip, with the assembly comprising a bearing component including an inner semi-spherical bearing surface for receiving a femoral ball and an outer surface attachable to a shell component for attachment to an acetabulum to replace a natural hip socket, the shell component including an inner surface defining a hemispherical cavity for receiving the outer semi-spherical surface of the bearing component therein, the positioning apparatus comprising
   a handle having a longitudinal axis,
   a split head divided into first and second gripping elements that jointly form a gripping surface to engage the inner semi-spherical cavity bearing surface of the bearing component, and wherein one of said first and second gripping elements is attached to said handle,
   a spring biased to urge separation of the first and second gripping elements,
   means for moving the first and second gripping elements closer together against said spring to allow positioning of the split head in contact with the inner semi-spherical surface of the bearing component,
   wherein an outer surface of a portion of the split head is hemispherically configured when the gripping means are moved together, and
   wherein the first and second gripping elements have offset gripping surfaces thereon and are substantially mirror images formed by hemisection of the hemispherical configured split head to provide substantial coincident mating with the internal semi-spherical bearing surface.

2. The apparatus of claim 1 wherein the gripping surface comprises a first gripping ridge defined in each of the split heads to promote engagement of the bearing component.

3. The apparatus of claim 2 further comprising a second gripping ridge defined in the split head to promote engagement of bearing components sized smaller than bearing components engaged by the first gripping ridge.

4. The apparatus of claim 3 wherein the first and second gripping ridges respectively encircle the split head.

5. The apparatus of claim 1 wherein the first gripping element of the split head is fixedly held relative to the handle, and the second gripping element is movable with respect to the handle.

6. The apparatus of claim 5 wherein said moving means comprises a lever arm attached to the second gripping element of the split head.

7. The apparatus of claim 5, wherein there is a pivot pin on the first gripping element and the second gripping element is pivotally mounted thereon.

8. The apparatus of claim 1, further comprising means for fixing the split head to the handle at an angle with respect to the longitudinal axis of the handle.

9. The apparatus of claim 8, wherein the fixing means comprises external threads defined on the handle for threaded engagement with a declination adapter that cooperates with internal threads defined in the split head.

10. The apparatus of claim 9, wherein the declination adaptor further comprises a body defining internal threads for threaded engagement of the external threads of the handle, and external threads for threaded engagement of the internal threads of the split head, with the external threads of the body directed at a non-parallel angle relative to the internal threads of the body.

11. An apparatus for positioning a prosthetic cup assembly in a patient, with the cup assembly including an inner surface defining a semi-spherical cavity therein, the positioning apparatus comprising
   a handle having a longitudinal axis,
   a gripping head insertible into the semi-spherical cavity of the cup assembly, the gripping head having at least two separable members, said members having at least a quarter-spherical external surface with offset gripping surfaces thereon the separable members moveable apart from each other to engage the inner semi-spherical cavity surface of the cup assembly
   means for coupling the gripping head to the handle, and
   means for alternately separating and unifying the separable members to have their quarter-spherical surfaces to respectively and coincidentally engage the inner semi-spherical cavity surface of the cup assembly and disengage from the inner semi-spherical cavity surface of the cup assembly to release the cup assembly.

12. The apparatus of claim 11, wherein the separating and unifying means includes at least one spring biased to urge separation of the separable members.

13. The apparatus of claim 12, wherein the separating and unifying means includes a lever arm attached to one of the at least two separable members, the lever arm movable to oppose the spring bias and move the separable members closer together.

14. The apparatus of claim 11, wherein the gripping surface includes a first gripping ridge, the gripping ridge being defined to encircle the gripping head and to hold the cup assembly.

15. The apparatus of claim 14, wherein the quarter-spherical surfaces of each of the separable members is a first impact surface defined to lie substantially perpendicular to the gripping ridge.

16. The apparatus of claim 11, wherein the means for coupling the gripping head to the handle comprises a fixed coupling of one of the at least two separable members to the handle and a pivot connection of the other of said at least two separable members.

17. The apparatus of claim 16, wherein the fixed coupling connects the one of the at least two separable members to the handle at an acute angle with respect to the longitudinal axis of the handle.

18. An apparatus for positioning a prosthetic cup assembly in a patient, with the cup assembly including an inner surface defining a semi-spherical cavity therein, the positioning apparatus comprising a handle having a longitudinal axis, a gripping head insertible into the semi-spherical cavity of the cup assembly, the gripping head having at least two separable members with spherical quadrant surface that can be moved apart from each other to engage the inner semi-spherical cavity surface of the cup assembly means for coupling the gripping head to the handle comprising:

a first set of cooperating screw threads to fixedly attach one of the at least two separable members to the handle, a pivot pin on one of said at least two separable members, another of said at least two separable members pivotally coupled to said pivot pin.

means for alternately separatingly pivoting said other of said at least two separable members with respect to said one of said at least two separable members to respectively engage the inner semi-spherical cavity surface of the cup assembly and for bringing the two separable members toward each other to disengage the gripping head from the inner semi-spherical cavity surface of the cup assembly and release the cup assembly.

19. The apparatus of claim 18, wherein the separating means includes at least one spring biased to urge separation of the separable members.

20. The apparatus of claim 19, wherein the separating and bringing together means includes a lever arm attached to the other of said at least two separable members, and wherein the lever arm is movable to oppose the spring bias and move the separable members closer together.

21. The apparatus of claim 18, wherein the gripping head includes a first gripping ridge, the gripping ridge being defined to encircle the gripping head and to hold the cup assembly.

22. The apparatus of claim 21, wherein the gripping head includes a first impact surface defined to lie substantially perpendicular to the gripping ridge.

23. The apparatus of claim 22, wherein the gripping head includes a second gripping ridge spaced from the first gripping ridge and with a perimeter smaller than a perimeter of the first gripping ridge to hold a cup assembly of smaller size than the said cup assembly.

24. The apparatus of claim 23, wherein there is a second impact surface that lies substantially perpendicular to the second gripping ridge.

25. The apparatus of claim 18 further comprising a declination adaptor containing one of the cooperating screw threads and positionable between one of the at least two split heads and the handle to angle one of said at least two split heads relative to the axis of the handle.

26. The apparatus of claim 25, wherein the declination adaptor further comprises a body defining internal threads for threaded engagement with external threads of the handle, and external threads for threaded engagement with internal threads of one of said at least two split heads, and wherein the external threads of the body is directed at a non-parallel angle relative to the internal threads of the body.

* * * * *